United States Patent [19]

Hurwitz

[11] Patent Number: 4,977,897
[45] Date of Patent: Dec. 18, 1990

[54] AMNIOCENTESIS NEEDLE WITH IMPROVED SONOGRAPHIC VISIBILITY

[76] Inventor: Robert Hurwitz, 2310 Tustin Ave., Newport Beach, Calif. 92660

[21] Appl. No.: 233,073

[22] Filed: Aug. 17, 1988

[51] Int. Cl.$^5$ ............................................... A61B 8/14
[52] U.S. Cl. .............................. 128/662.05; 128/763
[58] Field of Search ............ 128/329 R, 348.1, 653 R, 128/660.1, 662.05, 760, 763

[56] References Cited

U.S. PATENT DOCUMENTS

| | | | |
|---|---|---|---|
| 4,058,114 | 11/1977 | Soldner | 128/622.05 |
| 4,308,875 | 1/1982 | Young | 128/753 |
| 4,401,124 | 8/1983 | Guess et al. | 128/622.05 |
| 4,428,379 | 1/1984 | Robbins et al. | 128/653 R |
| 4,582,061 | 4/1986 | Fry | 128/329 R |

OTHER PUBLICATIONS

J. Ultrasound Med. 5.000-000, "Laboratory Assessment of Ultrasonic Needle and Catheter Visualization" by John P. McGahan, M.D., Jul. 1986, 5 pages.

*Primary Examiner*—Max Hindenburg

[57] ABSTRACT

Disclosed is a medical cannula or amniocentesis needle of improved sonographic visibility. The invention comprises a needle or cannula having one or more sounding apertures formed therein. The diameter of each sounding aperture is substantially equal to a predetermined wavelength of an incident ultrasonic beam. As a result, the beam will diffract upon striking the sounding aperture and the resultant echo will ddiffuse isotropically therefrom, thereby improving the ultrasonic detectability thereof.

22 Claims, 1 Drawing Sheet

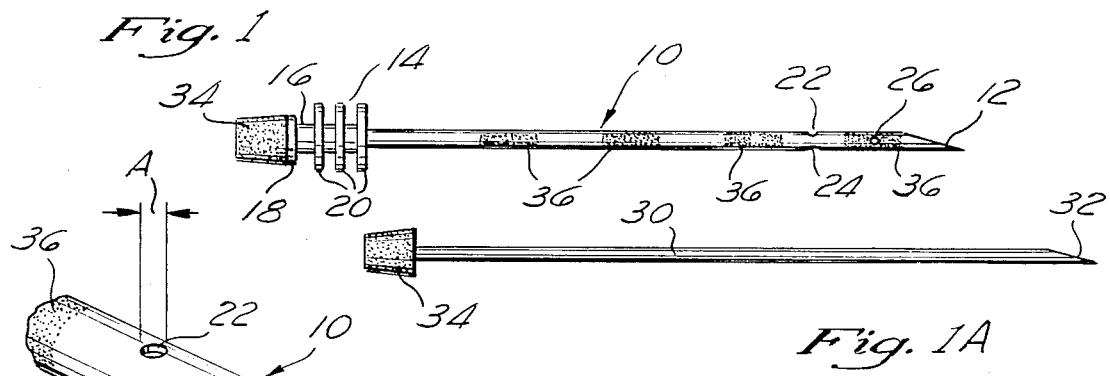
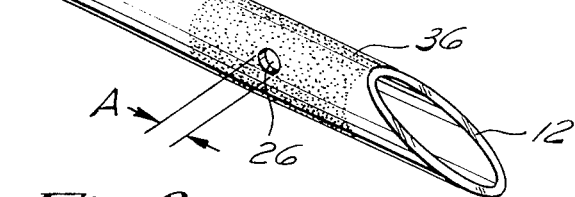
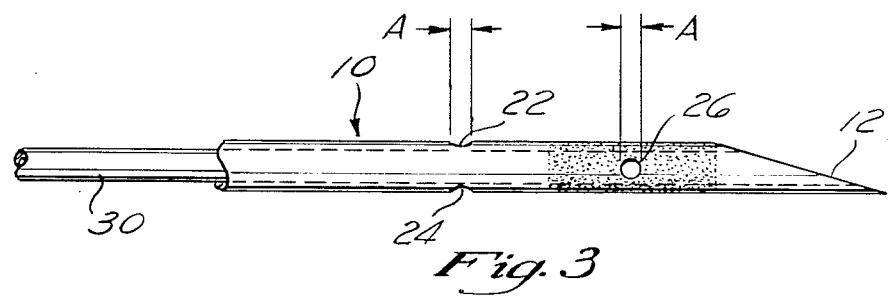
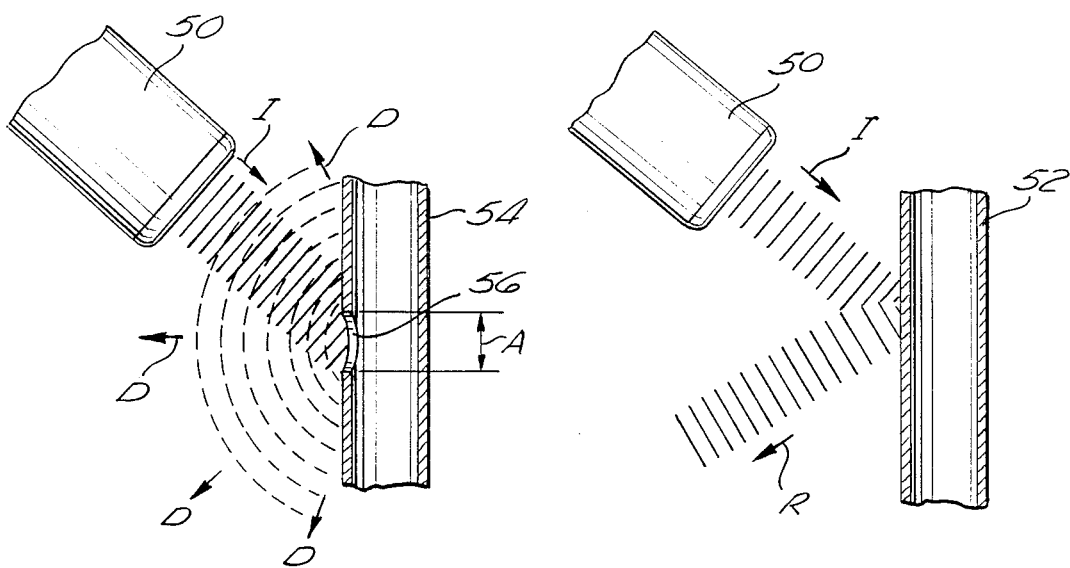

AMNIOCENTESIS NEEDLE WITH IMPROVED SONOGRAPHIC VISIBILITY

BACKGROUND OF THE INVENTION

This invention relates generally to the medical arts and more particularly to a needle or other tubular cannula having improved sonographic visibility.

The present invention is particularly suited for use in amniocentesis procedures and will be described herein as an improved "amniocentesis needle". It must be appreciated, however, that the means for improving acoustical detectability of the present invention may have broad applicability and may find utility in connection with virtually any needle, tube, catheter, cannula, trocar, or object wherein improved ultrasonic visibility is desired Specific examples of devices other than amniocentesis needles wherein the acoustical improvements of the present invention may be applicable include, but are certainly not limited to, various biopsy needles, aspiration cannulae, trocars, insertable scopes, surgical instruments, drug-containing implant devices, and cardiovascular catheters of the type routinely placed by echocardiographic guidance.

Referring specifically to amniocentesis procedures, the safety and efficiency of such procedures has been substantially improved in recent years by the application of real time ultrasonic imaging as a means for monitoring the percutaneous transabdominal insertion and intrauterine placement of the aspiration needle. Such ultrasonic imaging and guidance provides a safe and non-invasive means for ensuring proper placement of the needle to avoid inadvertant aspiration of blood from the uterus or placenta or damage to the fetus The proper placement of the needle prior to aspiration is particularly important in that any contamination of the amniotic fluid sample by blood from the uterus or placenta may render the sample unacceptable for analysis, thus requiring that the entire procedure be repeated, thereby multiplying the attendant risk of injury to the mother and/or fetus. Another benefit derived from routine ultrasonic guidance has been a significant decrease in the incidence of fetal injury. Most injuries to the fetus during amniocentesis have previously occurred due to direct traumatization of the fetus by the aspiration needle. Thus, the ability to carefully monitor placement of the needle tip relative to the fetus is a key factor in avoiding injury to the fetus. Unfortunately, the acoustical properties and resultant "imageability" of the commonly used amniocentesis needles are generally less than optimal for the reasons hereinafter discussed.

Today, most aminocentesis procedures are routinely carried out using standard 20-gage "spinal" needles of the type generally used to perform lumbar puncture and aspiration of cerebrospinal fluid The use of such spinal needles to perform amniocentesis procedures is, however, associated with several deficiencies. First, the single opening at the end of the standard spinal needle is known to become easily occluded by solid materials commonly entrained within the amniotic fluid. In practice, such occlusion of the needle tip generally requires prolongation of the procedure while the attending physician endeavors to reposition the needle tip. If such attempts are unsuccessful, it may then be necessary to fully repeat the percutaneous puncture and transabdominal placement of the needle so as to repeat the aspiration of the amniotic fluid sample Second, the smooth polished surface of the standard spinal needle is generally difficult to image by ultrasonic means. This is due to the smooth shaft of the needle typically reflecting the incident ultrasound beam in a non-diffracted, unidirectional, geometric manner. Thus, unless the receiving transducer element is precisely positioned in the path of the geometrically reflected beam, such beam will avoid the transducer and thus escape visualization by the imaging apparatus.

In contrast to the smooth surface of the needle shaft, the beveled tip of the standard spinal needle is usually detected by the imaging equipment because the incident ultrasound beam tends to be diffracted, rather than simply reflected, from the roughened edge and angular disposition of the beveled needle tip. Such diffraction of the incident beam from the beveled needle tip gives rise to a diverging accoustical reflection or echo. As a result of such divergence, it is most probable that some portion of the reflected beam will arrive at the desired transducer element Such diffracted echos are, however, associated with at least one drawback in that they are generally bright "blooming" echos which frequently exhibit phantom displacement from the actual position of the needle tip.

In addition to the above-described problems stemming from the poor ultrasonic detectability of the standard spinal needle, other problems are typically associated with the ultrasonic imaging of all amniocentesis needles. Specifically, ultrasonic imaging systems which employ single-element, fixed focus transducers generally emit incident beams of fixed focal depth (i.e. short range =1–4 cm, medium range =4–8 cm, and long range =6–12 cm) In amniocentesis procedures, the desired focal depth is generally within the "medium range" as the incident beam must travel through 3 to 4 centimeters of soft tissue, i.e. skin, muscle, and fat before reaching the amniotic cavity. At such depth, the focal region is normally less than 10 mm in diameter Thus, if the shaft of the needle is not precisely positioned within such focal region, any acoustical reflection or echo emanating therefrom will be of diminished amplitude and, thus, will be difficult to image. For this reason, poor focusing of a standard smooth walled needle may tend to further complicate the problems created by the non-diffracted, geometric reflection of the incident beam from the smooth needle shaft.

More complex ultrasonic imaging systems employed today incorporate annular or linear array technology wherein multiple independent transducer elements are arranged concentrically or linearally about a central transducer element. The formation and linear focus of the incident beam are achieved by pulsing the individual transducer elements in a time delayed or phased fashion. Thereafter, the electronic signals generated by the returning echos are received and combined using similar timed delays. By such method, these phased array systems are capable of being electronically and dynamically focused in two dimensions without mechanical movement or adjustment of the transducer head. However, because such electronic focusing is generally limited to only two dimensions, the focal depth continues to be set by specific mechanical lenses placed on each element of the transducer. Thus, any disparity between the position of the needle and the preset focal depth will remain problematic, even though a dynamically focusable linear or annular phased array system is employed.

Furthermore, linear phased array imaging systems are known to produce spurious echos which may interfere with visualization of the amniocentesis needle. These spurious echos, when passing through tissue, are of generally low amplitude and may be easily differentiated from anatomical structures. However, amniotic fluid differs from soft tissue structures in that it tends to "fill in" with numerous high amplitude spurious echos The transmission of such high amplitude spurious echos within the fluid further complicates the desired visualization of the needle while it is positioned within the amniotic cavity.

Thus, because of the poor echogenicity of the standard smooth-walled spinal needle, in conjunction with the various focusing problems inherent in all ultrasonically guided amniocentesis procedures, there exists a present need in the art for an improved amniocentesis needle which is readily visible by sonographic means.

Previous attempts have been made to improve the sonographic visibility or echogenicity of certain amniocentesis needles; however, such efforts have failed to produce a truly optimal amniocentesis needle. As a result, the medical profession has largely failed to adopt the marginally "improved" amniocentesis needles, opting instead to continue using the standard smooth-walled spinal needle. In fact, it is estimated that more than ninety percent of the amniocentesis procedures currently performed in the U.S. continue to employ standard 20 or 22 gage spinal needles, despite their poor imageability.

Most of the prior art attempts to improve the sonographic visibility of smooth walled spinal needles have involved roughening or texturing the outer surface of the needle in order to promote some diffraction of the echoing beam. Specifically, it has been found that sonographic visibility of the needle shaft may be improved by roughening or scoring the outer surface of the needle itself or by roughening the surface of a solid stylet which is disposed axially within the lumen of the needle. While such roughening or scoring of the needle/stylet may somewhat improve the ultrasonic detectability of the needle by causing diffraction of the echoing beam, the process of scoring or roughening the needle surface further adds to the cost of manufacturing. Also, it should be recognized that a scored or roughened needle surface may complicate percutaneous insertion and/or subsequent passage of the needle to its desired position.

Examples of needles/stylets having scored or roughened outer surfaces include those described in U.S. Pat. No. 4,582,061 (Fry) as well as some of those described in the publication entitled "Laboratory Assessment of Ultrasonic Needle and Catheter Visualization", by McGahan, John P., J. Ultrasound Med., (July 1986).

Apart from these prior efforts to improve the ultrasonic imageability of amniocentesis needles, other improvements have been developed with the intent of avoiding possible occlusion or clogging of the needle tip during aspiration. One such "improved" amniocentesis needle is disclosed in U.S. Pat. No. 4,308,875 (Young). Such improved needle comprises a hollow needle having a blunt round non-cutting tip with multiple communicating side holes formed in the distal 1 cm of the cannula. A solid stylet, having a sharpened distal tip, is positionable within the lumen of the needle such that the sharpened distal tip of the stylet protrudes beyond the distal tip of the needle. This protruding portion of the stylet provides the necessary cutting tip for penetration of the skin, fascia, and underlying structures. The blunt tip of the cannula disposed about the stylet does not cut and, therefore, must be thrust through the tissue as the cannula/stylet assembly is inserted. Following withdrawal of the stylet, fluid may be aspirated through the cannula. The purported advantage of the side holes is to facilitate uninterrupted withdrawal of amniotic fluid without obstruction or clogging.

SUMMARY OF THE INVENTION

The present invention provides a medical cannula of vastly improved sonographic visibility. The means by which the sonographic visibility of the cannula is improved comprises one or more specifically sized "sounding apertures" capable of causing an incident ultrasonic beam of known wavelength to diffract, thereby giving rise to a diffuse and/or divergent acoustical echo of improved detectability.

In accordance with the invention, there is provided an improved medical cannula having a plurality of specifically sized sounding apertures extending transversely through the cannula wall. The diameter of each aperture is essentially equal to the known wavelength of an incident ultrasonic beam. When the incident ultrasonic beam meets the specifically sized aperture, the echo thereby formed will constitute a series of diffraction waves or echos. Such diffraction waves or echos will diffuse isotropically as they travel away from the sounding aperture. In contrast to the specifically sized apertures of the present invention, the provision of other apertures which are not specifically sized (e.g. those which are significantly larger or smaller than the wavelength of the incident ultrasound beam) will do little or nothing to improve the sonographic visibility of the cannula. Indeed, unless the diameter of the sounding aperture is substantially equal to the wavelength of the incident beam, the returning waves or echos will not be sufficiently diffracted or diffused to bring about the desired degree of improvement in sonographic visibility. Thus, it is only through the provision of specifically sized sounding aperture(s) that the cannulae of the present invention are endowed with substantially improved acoustical properties.

Further, in accordance with the invention, there is provided an amniocentesis needle having at least one sounding aperture of the foregoing character positioned near the sharpened/beveled distal tip of the needle so as to improve the sonographic visibility thereof. The diameter of each sounding aperture will be essentially equal to the known wavelength of an incident ultrasound beam. Accordingly, since 3.5 MHz ultrasonic transducers are routinely used in the real time ultrasound monitoring of amniocentesis procedures, the diameter of the sounding aperture(s) will be equal to 0.44 mm which is the known wavelength of the standard 3.5 MHz transducer as propagated in soft tissues. Other transducers of known wavelength may, of course, be employed and the diameter of the sounding aperture(s) will be accordingly sized to correspond therewith.

In accordance with yet another aspect of the invention, a plurality of sounding apertures may be positioned in the approximate distal 2 cm of the cannula or needle so as to provide for clear visualization and monitoring of the distal portion of the sharpened distal tip.

In accordance with yet another aspect of the invention, each sounding aperture formed in the amniocentesis needle or cannula will be carefully machined in an annular configuration so as to be as concentric as possible and to eliminate burrs, slivers, or cratering.

In accordance with a still further aspect of the invention an amniocentesis needle or cannula which incorporates the specifically sized sounding apertures of the present invention may be provided with a correspondingly sized and configured ground solid stylet disposable therewithin. Such stylet will be specifically sized and configured to be axially slidable within the lumen of the needle or other cannula. The tip of the amniocentesis needle alone may be sufficiently sharpened to penetrate the soft tissue. Thus, the stylet will be preferably positioned therewithin solely to prevent undesired entry of tissue and/or fluids into the lumen of the needle. Accordingly, the preferred stylet will, when disposed within the lumen of the needle, lie flush with the distal tip thereof and will not substantially protrude or extend therebeyond.

The principal object of the invention is to provide various medical cannulae having improved sonographic visibility.

Another object of the invention is to minimize the risk of injury to the mother and/or fetus during amniocentesis procedures by providing an amniocentesis needle having improved ultrasonic visibility.

A further object of the invention is to provide a novel and heretofore unknown means of improving the sonographic visibility of various medical devices, instruments, and the like.

Further objects and advantages will become apparent to those skilled in the art upon reading and understanding of the following detailed description and the accompanying drawings.

BRIEF DESCRIPTION OF THE DRAWINGS

FIG. 1 is an elevational view of a preferred amniocentesis needle of the present invention having a solid stylet wire axially disposed therewithin;

FIG. 1A is an elevational view of the solid stylet wire axially disposed within the amniocentesis needle shown in FIG. 1;

FIG. 2 is a perspective view of the distal tip of a preferred amniocentesis needle of the present invention;

FIG. 3 is a cutaway elevational view showing the distal portion of a preferred amniocentesis needle of the present invention having a solid stylet axially disposed therewithin;

FIG. 4 is a schematic representation of an ultrasonic beam being diffracted by a specifically sized side hole of an amniocentesis needle of the present invention; and FIG. 5 is a schematic representation of an ultrasonic beam being geometrically reflected from the smooth side wall of a standard needle.

DETAILED DESCRIPTION OF THE PREFERRED EMBODIMENT

The accompanying drawings are provided solely for the purpose of illustrating a presently preferred embodiment of the invention and are not intended to limit its scope in any way.

FIGS. 1-3 show the external configuration of a preferred amniocentesis needle of the present invention while FIGS. 4 and 5 illustrate the means by which the precise side hole sizing concept of the present invention provides improved sonographic visibility.

Specifically, referring to FIGS. 1-3, the amniocentesis needle comprises a cannula body 10 having a beveled distal tip 12 and a proximal connecting hub 14 formed on opposite ends thereof. The cannula body 10 of the needle will generally be of appropriate length and diameter to effect the desired percutaneous intrauterine insertion of the needle. Accordingly, in this preferred embodiment, the cannula portion 10 of the needle is approximately 3.5 inches in length and is formed of either thin wall 22-gage cannula stock (0.280 inch [7.11 mm]O.D.) or thin wall 20-gage cannula stock (0.355 inch [9.02 mm]O.D.). Of course, it is preferable that the cannula be formed of medical grade materials such as those marketed as Superior "microbore" or Sterling "plug drawn". The beveled distal tip 12 of the needle is formed in the configuration of an "A" spinal bevel.

The proximal connecting hub 14 comprises a clear plastic "Matsuoka" type hub incorporating a proximally open-ended female connector 16 with a Leur lock flange 18 extending therearound. Three annular ribs 20 extend laterally around the outer wall of the female connector 16 so as to form convenient finger gripping surfaces whereby the needle may be firmly grasped by the operator during insertion and/or manipulation.

Four specifically sized sounding apertures 22, 24, 26 (fourth not shown) are formed through the wall of the cannula 10 near its distal tip 12 to improve the sonographic visualization of the distal portion of the needle during the amniocentesis procedure. Specifically, individual sounding apertures are formed through the top (22), bottom (24), right side (26), and left side (not shown) of the cannula body. Each aperture 22, 24, 26 is machined to a close tolerance such that the diameter of the aperture is essentially equal to the incident beam wavelength of a particular ultrasonic transducer. Such precise sizing of the sounding apertures 22, 24, 26 provides an amniocentesis needle having improved sonographic imageability by a specific corresponding ultrasound transducer frequency. In this preferred embodiment, the sounding apertures 22, 24, 26 are specifically sized for optimal visualization by a 3.5-MHz ultrasound transducer. The incident beam wavelength of the 3.5-MHz ultrasound transducer as propagated in soft tissues is known to be 0.44 mm. Thus, in this preferred embodiment, the sounding apertures 22, 24 26 are each machined to a diameter of 0.44+/-0.013 mm (0.0173+/-0.0005 inch). Other specific sounding aperture diameters will be provided in accordance with the table of Example 1.

EXAMPLE 1

| | EXAMPLE 1 | |
|---|---|---|
| Ultrasonic Transducer Frequency (MHz) | Incident Beam Wavelength (mm) | Desired Diameter of Sounding Aperture(s) (mm) |
| 1.0 | 1.54 | 1.54 |
| 2.25 | 0.68 | 0.68 |
| 3.5 | 0.44 | 0.44 |
| 6.0 | 0.26 | 0.26 |
| 7.5 | 0.21 | 0.21 |
| 10.0 | 0.15 | 0.15 |

In forming the sounding apertures 22, 24, 26 great care is taken to avoid imperfections such as burrs, slivers, or cratering. Any significant degree of ovality of the holes is not acceptable—perfect roundness is preferable. Thus, the incorporation of such specifically sized and configured sounding holes 22, 24, 26 renders the amniocentesis needle of the invention capable of heretofore unequaled sonographic visibility.

A solid stylet wire 30, shown separately in FIG. 1A, is axially disposable within the inner lumen of the needle. The stylet wire 30 is provided with a solid beveled tip 32 which corresponds in configuration to the "A" spinal bevel of the distal tip 12 of the needle. When the stylet wire 30 is axially disposed within the inner lumen of the needle, the beveled distal tip 32 of the stylet wire will reside fully within and flush with the open bevel tip 12 of the surrounding needle. A color coded obturator cap 34 is fixed to the distal end of the stylet wire 30 and is sized and configured to fully cover the open end of the female connector 16 so long as the stylet wire 30 is fully distally advanced into the inner lumen of the needle. By covering or capping the opening of the female connector 16 the obturator cap 34 will prevent airborne or other contaminants from entering the inner bore of the female connector 16 until such time as the obturator cap 34 and attendant stylet wire 30 have been withdrawn and removed.

The outer surface of the cannula body 10 is electropolished to a smooth finish and then chemically etched to form gauging marks 36 at one centimeter intervals along the longitudinal axis of the cannula body 10. Although chemical etching is the marking method of choice in this preferred embodiment, it must be appreciated that any other acceptable means of forming the visually discernable markings may be employed. Indeed, the chemical etching by which these gauging marks 36 are formed does not roughen the surface of the needle for purposes of improving sonographic visibility thereof. Such etching need only be deep enough to create a visually discernable surface mark and, in this preferred embodiment, does not alter the reflection of an ultrasonic beam in any way.

FIGS. 4 and 5 illustrate the means by which the specifically sized sounding holes 22, 24, 26 of the present invention give rise to optimal sonographic visualization of the needle tip. FIG. 5 shows an ultrasonic beam being geometrically reflected from the polished outer wall of a solid needle. Specifically, a 3.5-MHz transducer 50 is positioned in relation to a solid cannula 52 as shown. The incident ultrasonic beam emanating from the transducer 50 is indicated by arrow I. As shown, the incident beam I strikes the solid surface of the needle 52 and reflects geometrically therefrom as a single reflected beam indicated by arrow R. Because the transducer head 50 is positioned angularly with respect to the solid walled needle 52, the reflected beam R is not returned to the transducer head 50 and is thereby not detected by the transducer. Thus, the arrangement shown in FIG. 5 would not result in visualization of the solid walled needle 52 by the imaging equipment to which transducer head 50 is attached.

On the other hand, FIG. 4 shows the manner in which the specifically sized holes of the present invention will cause optimal diffraction of the echoing beam, thereby insuring that the returning echo will be received by the transducer head 50. Specifically, as shown in FIG. 4, the 3.5-MHz transducer head 50 is directed angularly toward the cannula 54. Cannula 54 is provided with a single side hole 56 extending through the smooth polished outer wall of the cannula 54. The diameter A of the hole 56 is substantially 0.44 mm. Since the wavelength of the incident beam I emanating from the 3.5-MHz transducer head 50 is known to be 0.44 mm, the diameter A of the hole 56 is substantially equal to such incident beam wavelength. Such specific sizing of hole 56 causes the incident beam to be diffracted as indicated by arrows D. Such diffracted echo beam will clearly return to transducer head 50 and, thus, will result in clear visualization of the cannula 54.

In accordance with the concept of the present invention, virtually any type of medical cannula may be provided with specifically sized sounding apertures for the purpose of improving the sonographic visibility thereof. Although the invention has been described herein with particular reference to a presently preferred embodiment, it will be appreciated that various alterations and modifications may be made to such embodiment without departing from the spirit and scope of the invention. For example, the angular formation and shape of the beveled distal tip of the amniocentesis needle may be altered to effect any desired cutting or penetration of tissue. Also, the solid inner stylet may be roughened or scored in accordance with the prior art for purposes of further enhancing the sonographic visibility of the needle/stylet combination. Additionally, any suitable type of connecting hub may be formed on the proximal end of the needle and such connecting hubs may be specifically adapted to effect connection to various types of receptacles and/or instruments. Accordingly, it is intended that any and all such modifications and alterations be included within the scope of the following claims and the equivalents thereof.

What is claimed is:

1. A cannula for use in medical procedures wherein ultrasonic imaging of the cannula is achieved by directing an incident ultrasonic beam of known wavelength against the cannula, said cannula comprising:

a generally tubular cannula body having a proximal end, a distal end, a generally cylindrical wall, and a hollow inner lumen extending axially therethrough;

at least one generally round sounding aperture formed in said cannula wall, the diameter of said sounding aperture being approximately equal to the known wavelength of said incident ultrasonic beam.

2. The cannula of claim 1 wherein the diameter of said sounding aperture is substantially 0.44 mm so as to be substantially equal to the wavelength of an incident beam which has a wavelength of 0.44 mm.

3. The cannula of claim 1 wherein the diameter of said sounding aperture is substantially 0.15 mm so as to be substantially equal to the wavelength of an incident beam which has a wavelength of 0.15 mm.

4. The cannula of claim 1 wherein the diameter of said sounding aperture is substantially 0.21 mm so as to be substantially equal to the wavelength of an incident beam which has a wavelength of 0.21 mm.

5. The cannula of claim 1 wherein the diameter of said sounding aperture is substantially 0.26 mm so as to be substantially equal to the wavelength of an incident beam which has a wavelength of 0.26 mm.

6. The cannula of claim 1 wherein the diameter of said sounding aperture is substantially 1.54 mm so as to be substantially equal to the wavelength of an incident beam which has a wavelength of 1.54 mm.

7. The cannula of claim 1 wherein a tissue penetrating bevel is formed on the distal end thereof.

8. The cannula of claim 1 wherein a connecting hub is formed on the proximal end thereof.

9. The cannula of claim 8 wherein said connecting hub is configured to permit fluidic attachment of a syringe thereto so as to permit withdrawal of a quantity of fluid proximally through the lumen of said cannula and into said syringe.

10. The cannula of claim 1 wherein said sounding aperture(s) is located within 2 cm of the distal end of the cannula.

11. The cannula of claim 1 wherein a plurality of said sounding apertures are formed within 2 cm of the distal end of the cannula.

12. The cannula of claim 1 further comprising:
a solid stylet having a proximal end, a distal end, and an outer surface, said stylet being sized and configured so as to be slidably axially disposable within the cannula lumen.

13. The cannula of claim 12 wherein said solid stylet, when fully slidably advanced into said cannula lumen, is axially coextensive therewith and resides therein such that the distal end of said solid stylet is flush with the distal end of the surrounding cannula.

14. An amniocentesis needle of improved sonographic visibility comprising:
a generally tubular needle body having a proximal end, a distal end, a generally cylindrical wall, and a hollow inner lumen extending axially therethrough;
a connecting hub formed on said proximal end;
a tissue penetrating bevel located on the distal tip of said needle and operative to effect transabdominal penetration and intraamnionic positioning of at least the distal end of the needle; and
at least one generally round sounding aperture formed in the needle wall, the diameter of said sounding aperture being substantially equal to an incident ultrasonic beam wavelength between 0.15 and 0.54 mm so as to improve the imagability of acoustical return signals which emanate from the needle wall when an incident ultrasonic beam having a wavelength substantially equal to the diameter of the diameter of said sounding apertures is directed against said needle wall.

15. The amniocentesis needle of claim 14 wherein the wavelength of said incident ultrasonic beam is substantially 0.44 millimeters and the corresponding diameter of said sounding aperture(s) is substantially 0.44 millimeters.

16. The amniocentesis needle of claim 14 wherein the wavelength of said incident ultrasonic beam is substantially 0.15 millimeters and the corresponding diameter of said sounding aperture(s) is substantially 0.15 millimeters.

17. The amniocentesis needle of claim 14 wherein the wavelength of said incident ultrasonic beam is substantially 0.21 millimeters and the corresponding diameter of said sounding aperture(s) is substantially 0.21 millimeters.

18. The amniocentesis needle of claim 14 wherein the wavelength of said incident ultrasonic beam is substantially 0.26 millimeters and the corresponding diameter of said sounding aperture(s) is substantially 0.26 millimeters.

19. The amniocentesis needle of claim 14 wherein the wavelength of said incident ultrasonic beam is substantially 0.68 millimeters and the corresponding diameter of said sounding aperture(s) is 0.68 substantially millimeters.

20. The amniocentesis needle of claim 14 wherein the wavelength of said incident ultrasonic beam is substantially 0.54 millimeters and the corresponding diameter of said sounding aperture(s) is substantially 0.54 millimeters.

21. The amniocentesis needle of claim 14 further comprising:
a solid stylet having a proximal end, a distal end, and an outer surface, said stylet being sized and configured so as to be slidably axially disposable within the cannula lumen.

22. The cannula of claim 21 wherein said solid stylet, when fully slidably advanced into said cannula lumen, is axially coextensive therewith and resides therein such that the distal end of said solid stylet is flush with the distal end of the surrounding cannula.

* * * * *